(12) United States Patent
May

(10) Patent No.: US 11,026,733 B2
(45) Date of Patent: Jun. 8, 2021

(54) SURGICAL SYSTEM AND METHOD

(71) Applicant: Warsaw Orthopedic, Inc., Warsaw, IN (US)

(72) Inventor: Jason M. May, St Johns, FL (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 178 days.

(21) Appl. No.: 16/289,229

(22) Filed: Feb. 28, 2019

(65) Prior Publication Data
US 2020/0275961 A1 Sep. 3, 2020

(51) Int. Cl.
*A61B 17/88* (2006.01)
*A61B 17/86* (2006.01)
*A61B 17/00* (2006.01)

(52) U.S. Cl.
CPC ............ *A61B 17/88* (2013.01); *A61B 17/863* (2013.01); *A61B 17/8605* (2013.01); *A61B 2017/00367* (2013.01); *A61B 2017/00477* (2013.01)

(58) Field of Classification Search
CPC .. A61B 17/8875; A61B 17/88; A61B 17/8891
See application file for complete search history.

(56) References Cited

U.S. PATENT DOCUMENTS

| 9,615,862 B1 | 4/2017 | Doubler et al. |
| 2011/0282398 A1 | 11/2011 | Overes et al. |
| 2012/0089150 A1* | 4/2012 | Smith ................ A61B 17/7076 606/104 |
| 2012/0296380 A1 | 11/2012 | Simonson |
| 2013/0012954 A1 | 1/2013 | Paroth et al. |
| 2014/0180298 A1 | 6/2014 | Stevenson et al. |

* cited by examiner

*Primary Examiner* — Andrew Yang
(74) *Attorney, Agent, or Firm* — Sorell, Lenna & Schmidt, LLP

(57) ABSTRACT

A surgical instrument includes a first member defining a passageway. The first member includes a first lock and a second lock. A second member is positioned in the passageway. A third member is coupled to the second member. The second member is movable relative to the first member to move the third member between a first position in which the first lock is spaced a first distance apart from the second lock, and a second position in which the first lock is spaced a reduced second distance apart from the second lock. Systems, spinal implants and methods are disclosed.

20 Claims, 11 Drawing Sheets

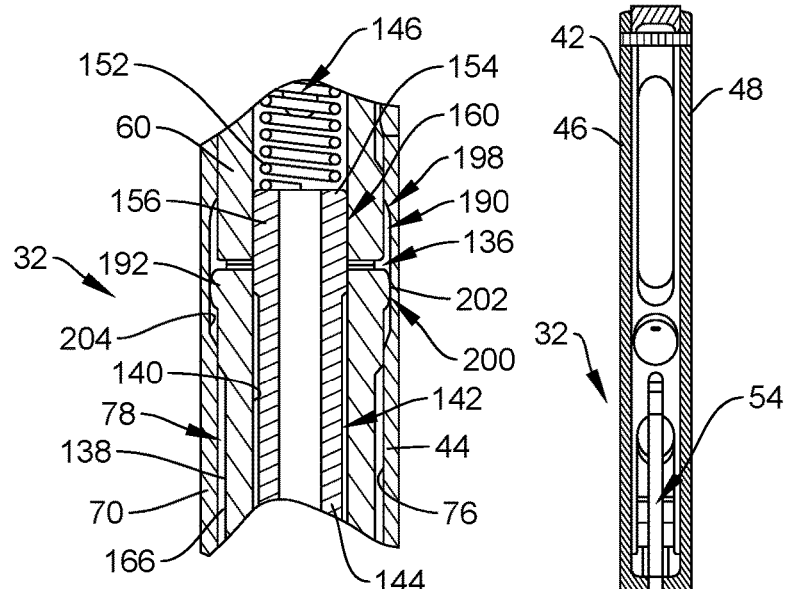
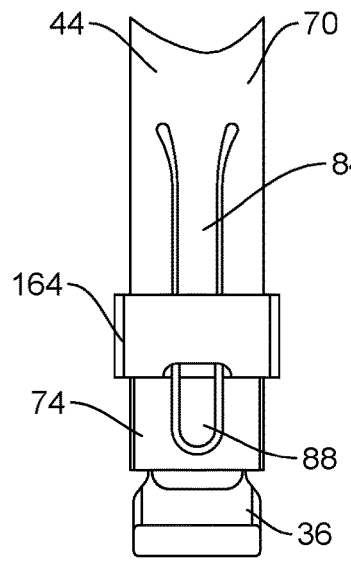
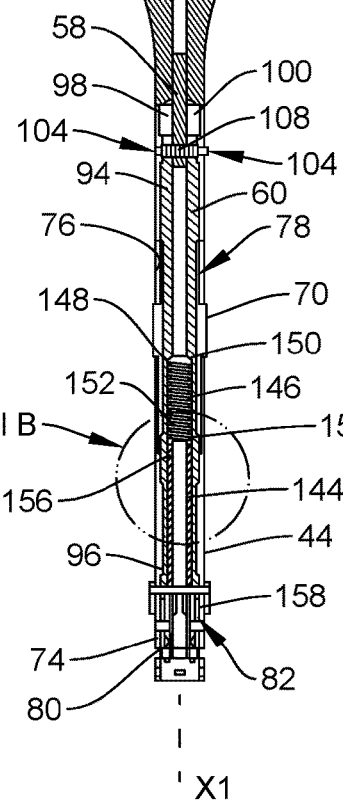
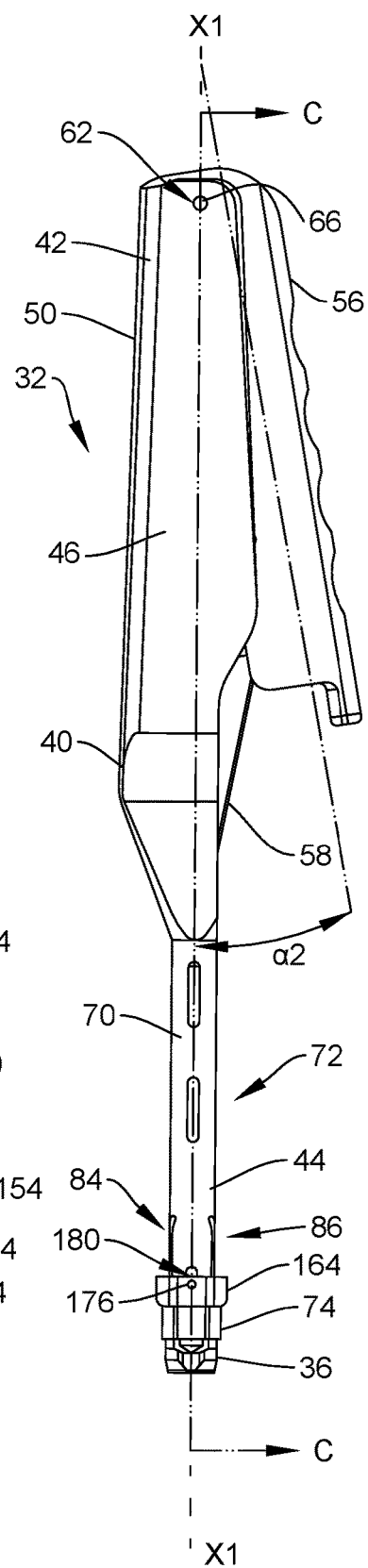
FIG. 15
FIG. 16
FIG. 14
FIG. 13

SURGICAL SYSTEM AND METHOD

TECHNICAL FIELD

The present disclosure generally relates to medical devices for the treatment of musculoskeletal disorders, and more particularly to a surgical system and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support vertebral members. During surgical treatment, one or more rods and bone fasteners can be delivered to a surgical site. The rods may be attached via the fasteners to the exterior of two or more vertebral members. Surgical treatment may employ surgical instruments and implants that are manipulated for engagement with vertebrae to position and align one or more vertebrae. This disclosure describes an improvement over these prior technologies.

SUMMARY

In one embodiment, a surgical instrument is provided. The surgical instrument includes a first member defining a passageway. The first member includes a first lock and a second lock. A second member is positioned in the passageway. A third member is coupled to the second member. The second member is movable relative to the first member to move the third member between a first position in which the first lock is spaced a first distance apart from the second lock, and a second position in which the first lock is spaced a reduced second distance apart from the second lock. In some embodiments, systems, spinal implants, spinal constructs and methods are disclosed.

In one embodiment, a surgical instrument is provided that includes an inserter body comprising a shaft defining a passageway. The shaft comprises a first spring tab and a second spring tab. A pusher is positioned in the passageway. A sleeve is coupled to the pusher. The pusher is movable relative to the inserter body to move the sleeve between a first position in which the first spring tab is spaced a first distance apart from the second spring tab, and a second position in which the first spring tab is spaced a reduced second distance apart from the second spring tab.

In one embodiment, a surgical system is provided. The surgical system comprises a surgical instrument comprising a first member defining a passageway and comprising a first lock and a second lock. The surgical instrument includes a second member positioned in the passageway and a third member coupled to the second member. The surgical system includes an implant comprising a head. The second member is movable relative to the first member to move the third member between a first position in which the first lock is spaced a first distance apart from the second lock to allow the head to be inserted into the passageway, and a second position in which the lock is spaced a reduced second distance apart from the second lock such that the locks engage the head within the passageway to fix the head relative to the shaft.

BRIEF DESCRIPTION OF THE DRAWINGS

The present disclosure will become more readily apparent from the specific description accompanied by the following drawings, in which:

FIG. 13 is a fourth side view of the surgical instrument shown in FIG. 1, with the surgical instrument in a second position;

FIG. 14 is a side, cross sectional view of the surgical instrument shown in FIG. 1 taken along lines C-C in FIG. 13;

FIG. 15 is an enlarged, cross section view of the surgical instrument shown in FIG. 1 at detail B in FIG. 14;

FIG. 16 is a side view of components of the surgical instrument shown in FIG. 1, with the surgical instrument in the second position;

DETAILED DESCRIPTION

Figure 1:
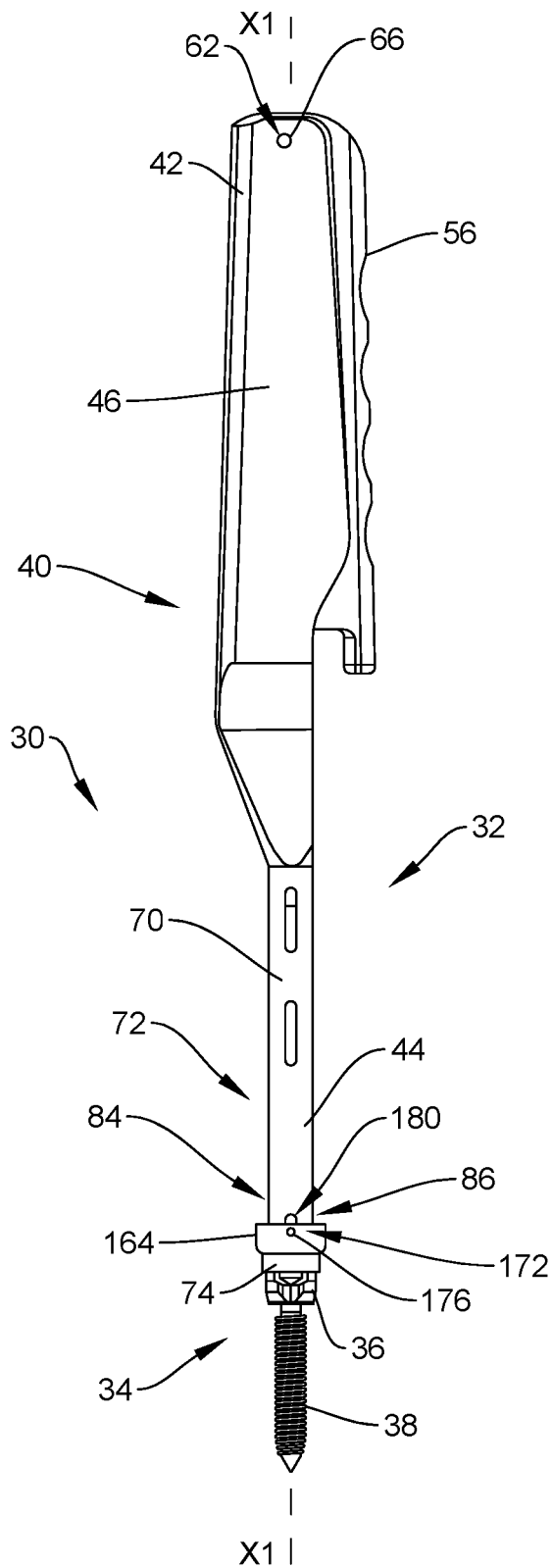
FIG. 1 is a side view of components of one embodiment of a surgical system including a surgical instrument and an implant.
Figure 2:
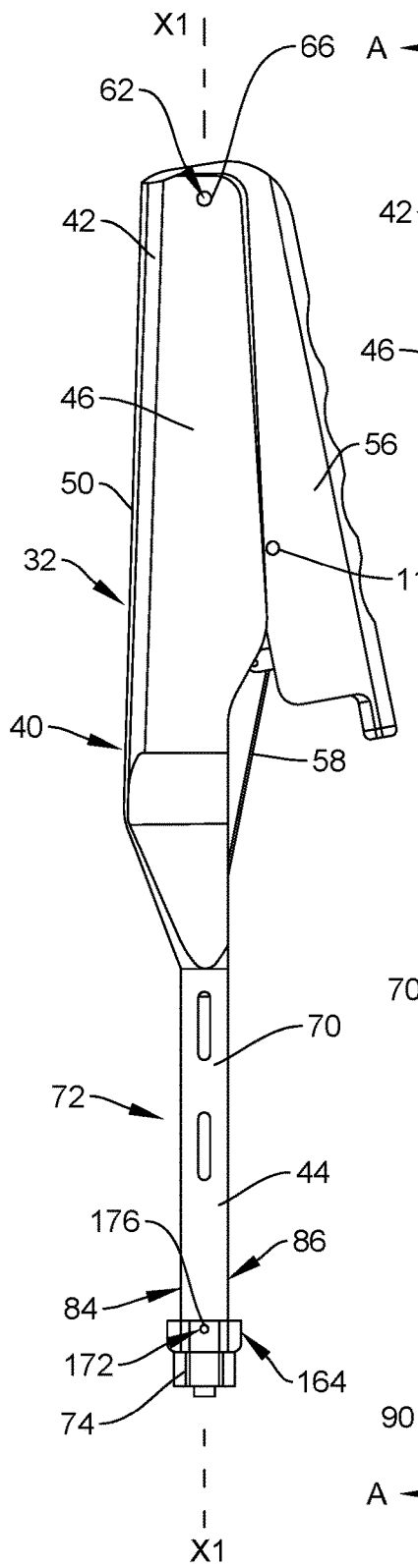
FIG. 2 is a first side view of the surgical instrument shown in FIG. 1.
Figure 3:
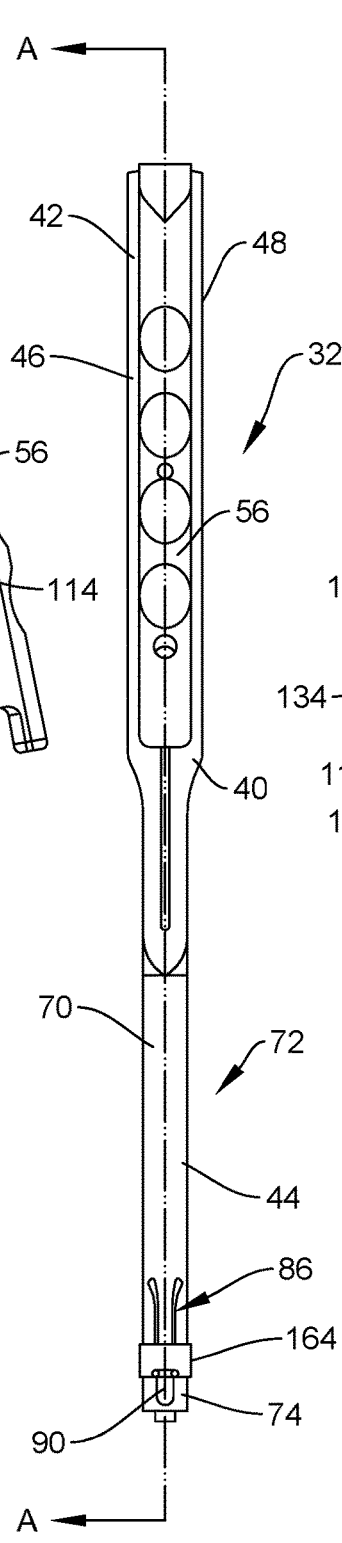
FIG. 3 is a second side view of the surgical instrument shown in FIG. 1.

The exemplary embodiments of the surgical system and related methods of use disclosed are discussed in terms of medical devices for the treatment of musculoskeletal disorders and more particularly, in terms of a surgical system and a method for treating a spine. In some embodiments, the systems and methods of the present disclosure comprise medical devices including surgical instruments and implants that are employed with a surgical treatment, as described herein, for example, with a cervical, thoracic, lumbar and/or sacral region of a spine.

In some embodiments, the present surgical system comprises a surgical instrument that includes an inserter body, a pusher, a plunger and a sleeve. The inserter body includes a first spring tab and the pusher includes a second spring tab. The plunger includes a raised surface that blocks the second spring tab from deflecting inwards, as discussed herein. The sleeve includes an internal surface that blocks the first spring tab from disengaging a portion of an implant, such as, for example, a tulip of a bone screw, as discussed herein.

In some embodiments, the surgical instrument comprises a handle coupled to the inserter body. The handle is coupled to the pusher by a link. A piston connects the handle with the link. The piston includes a spring, such as, for example, a canted coil spring. In some embodiments, the handle, the link, the piston, the spring and/or the plunger are part of a slider crank mechanism configured to move the surgical instrument between a first position (e.g., an open position), a second position (e.g., a secured position) and a third position (e.g., an attachment position), as discussed herein. In some embodiments, the handle includes a boss that allows the canted coil spring to be overcome by two handed force to facilitate moving the surgical instrument between the open position, the secured position and the attachment position, as discussed herein.

When the surgical instrument is in the first, open position, the canted coil spring is not engaged in any grooves of the piston and the handle is in a max open position. The plunger is in a down position, without the bone screw in place. The second spring tab is blocked from deflecting inwards, but the pusher is allowed to slide down. An internal bore in the inserter body allows the sliding of the pusher within the inserter body. The sleeve is in an up position such that the first spring tab is free, which allows the tulip to be inserted and removed. That is, the tulip of the bone screw can be inserted into a passageway of the inserter body when the surgical instrument in the first, open position. The tulip is removably positioned in the passageway until the surgical instrument moves from the first, open position to the second, secured position.

To move the surgical instrument from the first, open position to the second, secured position, the handle is squeezed to move the handle toward the inserter body to engage the canted coil spring into a square groove of the piston, which prevents the handle from moving back to the max open position (wherein the canted coil spring is not engaged in any grooves of the piston) without a high force. The plunger remains in the down position. The second spring tab is blocked from deflecting inwards, which blocks the pusher from sliding down to prevent unintentional activation of a lock mechanism, as discussed herein. The sleeve moves downwardly along the first tab to block the inserter body from disengaging the tulip such that the tulip is no longer removable from the passageway of the inserter body.

To move the surgical instrument from the second, secured position to the third, attachment position, the handle is squeezed to move the handle further toward the inserter body such that the canted coil spring moves from the square groove and into a tapered groove of the piston. As the canted coil spring moves from the square groove to the tapered groove, the canted coil spring changes shape to allow the handle to move back to the max open position (wherein the canted coil spring is not engaged in any grooves of the piston). The plunger moves from the down position to an up position. The second spring tab is free to deflect inwards to allow the plunger to activate the locking mechanism. The sleeve moves further down along the first tab to block the inserter body from disengaging the tulip such that the tulip is locked with the inserter body.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including a surgical instrument, implants, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-25, there are illustrated components of a surgical system, such as, for example, a spinal implant system 30.

The components of spinal implant system 30 can be fabricated from biologically acceptable materials suitable for medical applications, including metals, synthetic polymers, ceramics and bone material and/or their composites. For example, the components of spinal implant system 30, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 30 may have material composites, including the above materials, to achieve various desired characteristics such as strength, rigidity, elasticity, compliance, biomechanical performance, durability and radiolucency or imaging preference. The components of spinal implant system 30, individually or collectively, may also be fabricated from a heterogeneous material such as a combination of two or more of the above-described materials. The components of spinal implant system 30 may be monolithically formed, integrally connected or include fastening elements and/or instruments, as described herein.

Spinal implant system 30 is employed, for example, with a fully open surgical procedure, a minimally invasive procedure including percutaneous techniques, and mini-open surgical techniques to deliver and introduce instrumentation and/or one or more spinal implants, such as, for example, one or more components of a bone fastener, at a surgical site of a patient, which includes, for example, a spine. In some embodiments, the spinal implant can include one or more components of one or more spinal constructs, such as, for example, interbody devices, interbody cages, bone fasteners, spinal rods, tethers, connectors, plates and/or bone graft, and can be employed with various surgical procedures including surgical treatment of a cervical, thoracic, lumbar and/or sacral region of a spine.

Spinal implant system 30 includes a surgical instrument, such as, for example, a tulip head inserter 32 and an implant, such as, for example, a bone screw 34 including a head, such as, for example, a tulip head 36 and a shaft 38 configured to be bottom loaded into head 36 to connect shaft 38 with head 36, as discussed herein. Inserter 32 is configured to mount head 36 onto shaft 38 after shaft 38 has been implanted with tissue, such as, for example, bone. That is, inserter 32 can be used to grasp head 36 and then manipulate head 36 relative to implanted shaft 38 to mount head 36 onto shaft 38, as discussed herein.

Figure 5:
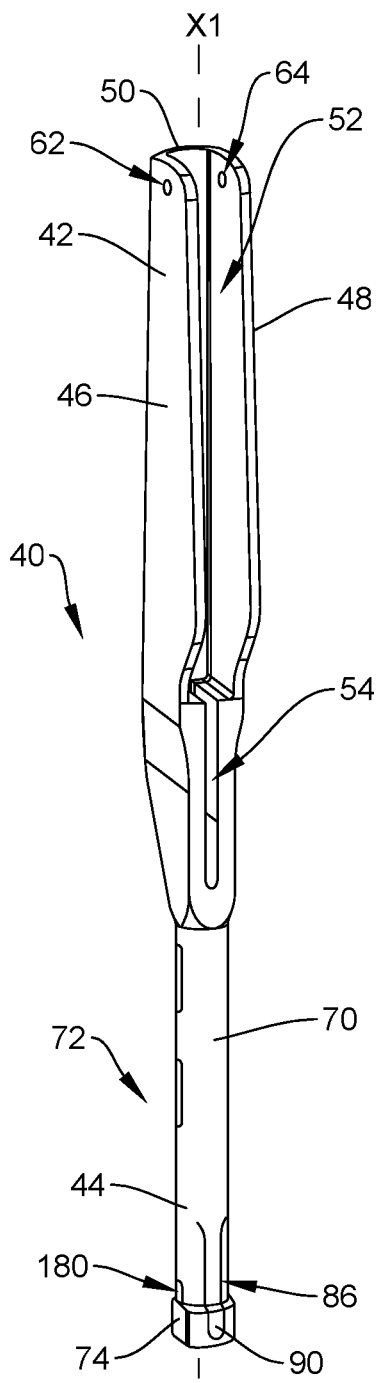
FIG. 5 is a perspective view of a first component of the surgical instrument shown in FIG. 1.

Inserter 32 includes a member, such as, for example, an inserter body 40 extending along a longitudinal axis X1 between an end 42 and an opposite end 44. End 42 includes a wall 46 that is spaced apart from a wall 48 by a wall 50, as best shown in FIG. 5. Walls 46, 48 extend parallel to one another and wall 50 extends transverse to walls 46, 48 to join wall 46 with wall 48. Inner surfaces of walls 46, 48, 50 define a cavity 52 and a slot 54 that is in communication with cavity 52. Cavity 52 extends parallel to axis X1 and is configured for disposal of a member, such as, for example, a handle 56, as discussed herein. Slot 54 extends parallel to axis X1 and is configured for disposal of a link 58 that connects handle 56 with a member, such as, for example, a pusher 60, as discussed herein. Wall 46 includes an aperture 62 and wall 48 includes an aperture 64 that is aligned with aperture 62 along an axis that extends perpendicular to axis X1. A pin 66 extends through apertures 62, 64 and a hole 68 that extends through a thickness of handle 56 to connect handle 56 with body 40 such that handle 56 is pivotable and/or rotatable relative to body 40 about pin 66 to move instrument 32 between a first position, a second position and a third position, as discussed herein. In some embodiments, cavity 52 and/or slot 54 may be disposed at alternate orientations, relative to axis X1, such as, for example, transverse, perpendicular and/or other angular orientations such as acute or obtuse, co-axial and/or may be offset or staggered.

End 44 includes a tubular wall 70 that defines a shaft 72. End 44 further includes an enlarged engagement portion 74 extending from a distal end of shaft 72. An inner surface 76 of wall 70 defines a passageway 78 configured for disposal of pusher 60, as discussed herein. An inner surface 80 of portion 74 defines a cavity 82 configured for disposal of head 36, as discussed herein. Cavity 82 has a maximum width or diameter that is greater than a maximum width or diameter of passageway 78 to accommodate head 36 within cavity 82. That is, the maximum width or diameter of cavity 82 is at least slightly greater than the maximum width or diameter of head 36 such that head 36 can be positioned within cavity 82. In some embodiments, passageway 78 and/or cavity 82 may have various cross section configurations, such as, for example, oval, oblong, triangular, rectangular, square, polygonal, irregular, uniform, non-uniform, variable, tubular and/or tapered.

End 44 includes a first lock, such as, for example, a spring tab 84 on a first side of wall 70 and a second lock, such as, for example, a spring tab 86 on an opposite second side of wall 70 such that an inner surface of spring tab 86 faces an inner surface of spring tab 84. Spring tabs 84, 86 are each defined by recesses that extend through a thickness of wall 70 and are each configured to deflect relative to wall 70 as inserter 32 is moved between the first, second and third positions, as discussed herein. Spring tab 84 has a distal end 88 in portion 74 that is configured to engage head 36 when head 36 is positioned in cavity 82 and spring tab 86 has a distal end 90 in portion 74 that is configured to engage head 36 when head 36 is positioned in cavity 82. In some embodiments, end 88 includes an inner surface that faces an inner surface of end 90. The inner surfaces of ends 88, 90 are each configured to directly engage head 36 when head 36 is positioned in cavity 82 to fix head 36 relative to body 40, as discussed herein. In some embodiments, at least one of spring tabs 84, 86 includes a protrusion projecting outwardly from the inner surfaces of ends 88, 90 such that the protrusions extend into corresponding recesses 92 in head 36 to enhance fixation of head 36 with body 40 when inserter 32 is in at least one of the first, second and third positions, as discussed herein.

Figure 4:
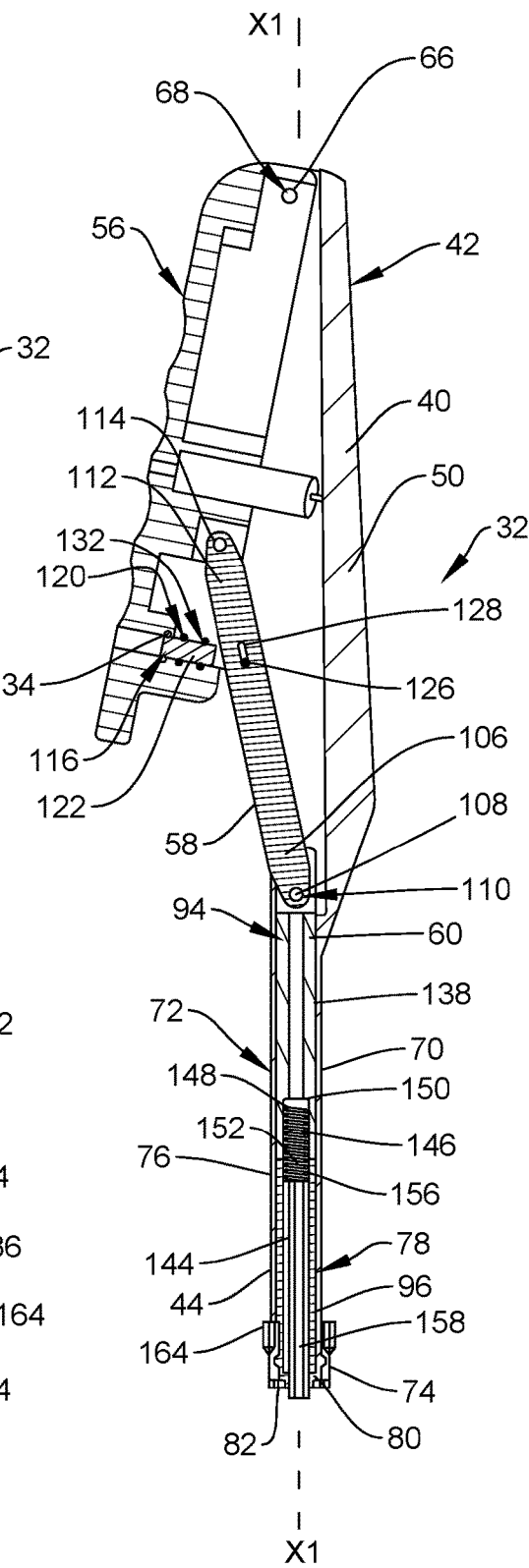
FIG. 4 is a side, cross section view of the surgical instrument shown in FIG. 1 taken along lines A-A in FIG. 3.
Figure 6:
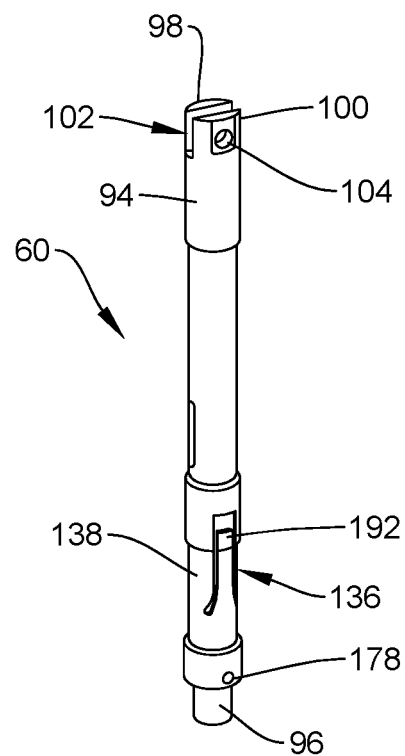
FIG. 6 is a perspective view of a second component of the surgical instrument shown in FIG. 1.
Figure 7:
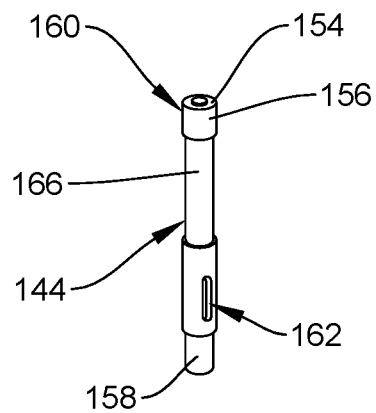
FIG. 7 is a perspective view of a third component of the surgical instrument shown in FIG. 1.
Figure 8:
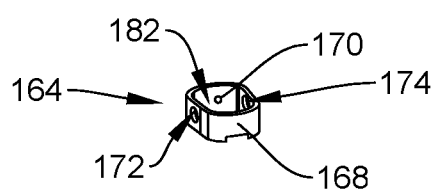
FIG. 8 is a perspective view of a fourth component of the surgical instrument shown in FIG. 1.

Pusher 60 is movably disposed in passageway 78 and extends between an end 94 and an opposite end 96. Pusher 60 is coaxial with axis X1 when pusher 60 is positioned in passageway 78. End 94 includes spaced apart arms 98, 100 that define a slot 102 therebetween, as best shown in FIG. 6. Arms 98, 100 each include an opening 104 that extends through a thickness of a respective one of arms 98, 100 such that openings 104 are in communication with slot 102. Openings 104 are aligned with one another along an axis that extends perpendicular to axis X1. An end 106 of link 58 is positioned in slot 102. A pin 108 extends through openings 104 and an opening 110 in end 106 to connect link 58 with pusher 60. An opposite end 112 of link 58 is connected directly with handle 56 via a pin 114 that extends through openings in end 112 and handle 56, as best shown in FIG. 4.

Figure 21:
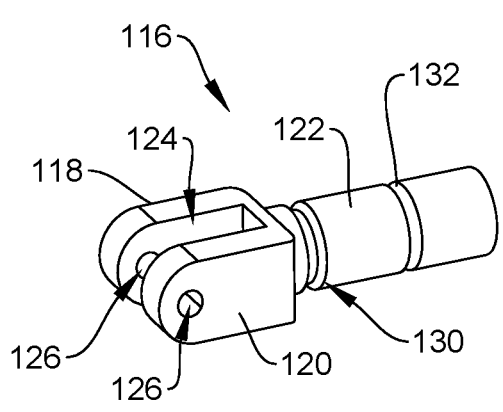
FIG. 21 is a perspective view of a component of the surgical instrument shown in FIG. 1.

A piston 116 indirectly connects handle 56 with pusher 60 via link 58. Piston 116 includes spaced apart arms 118, 120 and a shaft 122 that is coupled to arms 118, 120, as best shown in FIG. 21. Arms 118, 120 define a slot 124 therebetween. Arms 118, 120 each include an opening 126 that is in communication with slot 124. Openings 126 are aligned with one another along an axis that extends perpendicular to axis X1. A portion of link 58 is positioned in slot 124 and a pin 126 extends through openings 126 and an oblong opening 128 in link 58 to connect piston 116 with link 58. Shaft 122 includes a groove 130 and a groove 132 that is spaced apart from groove 130 along a length of shaft 122. In some embodiments, groove 130 has a tapered configuration and groove 132 has a square configuration. A spring, such as, for example, a canted coil spring 134 is positioned over shaft 122 and is configured for disposal in groove 130 or groove 132. In some embodiments, spring 134 moves between groove 130 and groove 132 as inserter 32 moves between the first position, the second position and the third position, as discussed herein.

End 96 includes a lock, such as, for example, a spring tab 136. Spring tab 136 is defined by a recess that extends through a thickness of a wall 138 of pusher 60 and is configured to deflect relative to wall 138 as inserter 32 is moved between the first, second and third positions, as discussed herein. An inner surface 140 of wall 138 defines a channel 142 configured for disposal of a member, such as, for example, a plunger 144 and a biasing member, such as, for example, a plunger spring 146. Plunger 144 is coaxial with axis X1 when plunger 144 is disposed in channel 142. Spring 146 is positioned between plunger 144 and includes an end 148 that engages a flange 150 of wall 138 to prevent spring 146 from moving past flange 150 in the direction shown by arrow D in FIG. 11. Spring includes an opposite end 152 that directly engages an end surface 154 of plunger 144 to move plunger 144 relative to pusher 60 in the direction shown by arrow E in FIG. 11 as inserter 32 moves between the first position, the second position and the third position, as discussed herein.

Plunger 144 extends between an end 156 and an opposite end 158. End 156 includes a raised surface 160 configured to block spring tab 136 from deflecting inwards, as discussed herein. End 158 includes an opening 162 extending through a thickness of plunger 144 and configured for disposal of a pin 176 to connect plunger 144 with a member, such as, for example, a sleeve 164, as discussed herein. Plunger 144 includes an undercut surface 166 between ends 156, 158 that allows spring tab 136 to deflect inwards as inserter 32 moves between the first, second and third positions, as discussed herein. In some embodiments, opening 162 is elongated and has an oblong shape to allow pin 176 to translate relative to plunger 144 in opposite axial directions along axis X1 as pusher 60 translates relative to plunger 144 in opposite axial directions along axis X1, as discussed herein.

Sleeve 164 includes a tubular wall 168 comprising an internal surface 170 configured to block spring tabs 84, 86 from disengaging head 36, as discussed herein. Sleeve 164 includes a pair of openings 172, 174 that each extend through a thickness of wall 168. A pin 176 extends through openings 162, 172, 174, an opening 178 in end 96 and an opening 180 in end 44 to connect sleeve 164 with body 40, pusher 60 and plunger 144 such that sleeve 164 translates relative to body 40 along axis X1 as pusher 60 translates relative to body 40 along axis X1, as discussed herein. In some embodiments, opening 180 is elongated and has an oblong shape to allow pin 176 to translate relative to shaft 72 in opposite axial directions along axis X1 as sleeve 164 translates relative to shaft 72 in opposite axial directions along axis X1. Surface 170 defines a bore 182 configured for disposal of shaft 72. An inner diameter of bore 182 is less than an outer diameter of portion 74 to prevent sleeve 146 from moving past portion 74 as sleeve 164 translates relative to body 40 along axis X1 in the direction shown by arrow E in FIG. 11. In some embodiments, opening 172, opening 174 and/or opening 178 have a diameter that is only slightly greater than the diameter of pin 176 such that pin 176 and sleeve 164 translate relative to shaft 72 in opposite axial directions along axis X1 as pusher 60 translates relative to shaft 72 in opposite axial directions along axis X1, as discussed herein.

Figure 25:
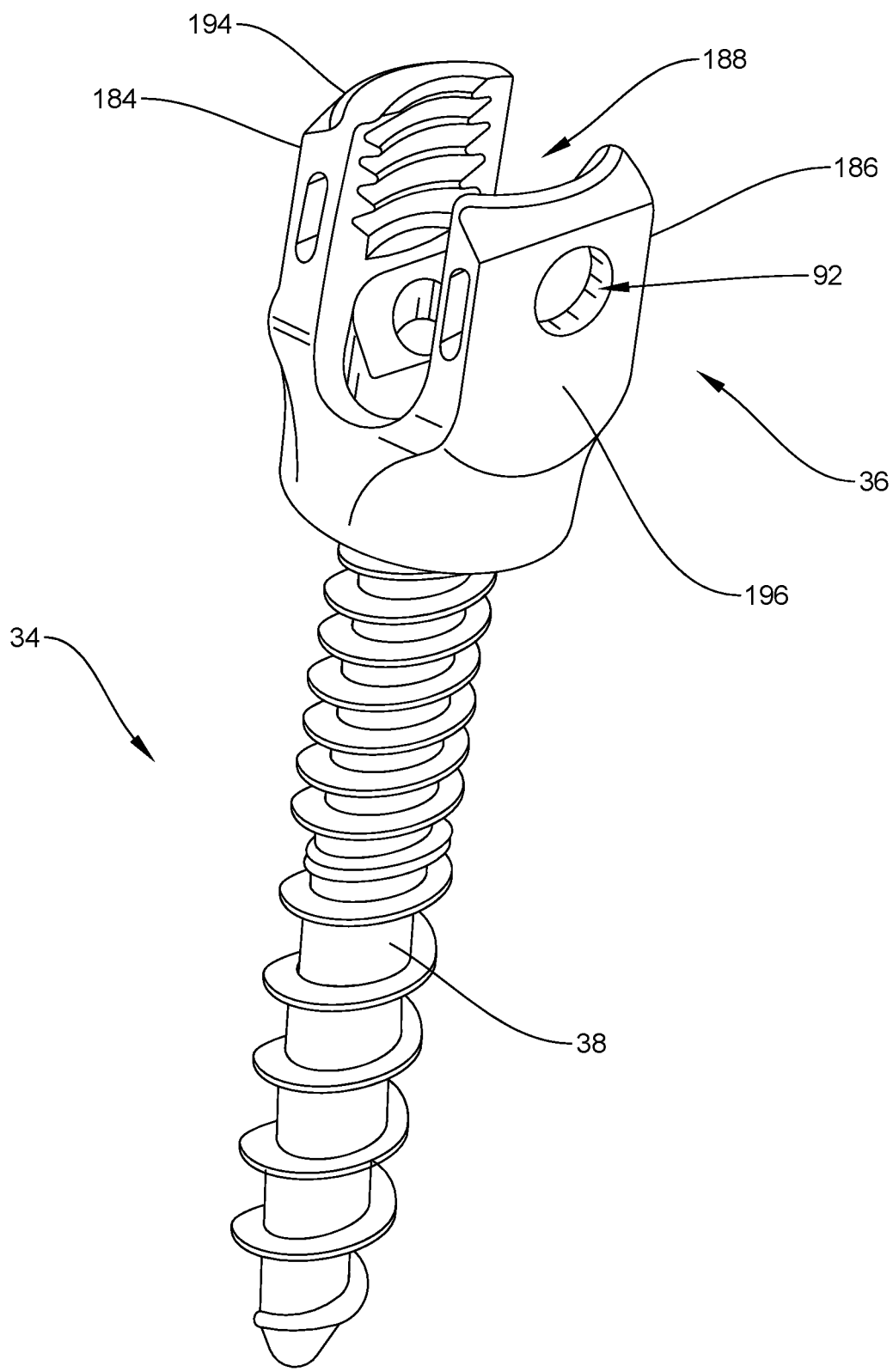
FIG. 25 is a perspective view of the implant shown in FIG. 1.

Head 36 includes a pair of spaced apart arms 184, 186, as best shown in FIG. 25. Arms 184, 186 include an inner surface that defines a U-shaped passageway 188. Passageway 188 is configured for disposal of a spinal construct, such as, for example, a spinal rod. In some embodiments, all or only a portion of passageway 188 may have alternate cross section configurations, such as, for example, oval, oblong, triangular, square, polygonal, irregular, uniform, non-uniform, offset, staggered, and/or tapered. In some embodiments, arms 184, 186 may be disposed at alternate orientations, relative to a longitudinal axis of screw 34, such as, for example, transverse, perpendicular and/or other angular orientations such as acute or obtuse, co-axial and/or may be offset or staggered. The inner surface of head includes a thread form configured for engagement with a coupling member, such as, for example, a set screw to fix a spinal rod positioned in passageway 188 relative to head 36.

Shaft 38 has a cylindrical cross-sectional configuration and includes an outer surface having an external thread form. In some embodiments, the external thread form may include a single thread or a plurality of discrete threads. In some embodiments, other engaging structures may be located on shaft 38, such as, for example, a nail configuration, barbs, expanding elements, raised elements and/or spikes to facilitate engagement of shaft 38 with tissue.

In some embodiments, all or only a portion of shaft 38 may have alternate cross section configurations, such as, for example, oval, oblong, triangular, square, polygonal, irregular, uniform, non-uniform, offset, staggered, undulating, arcuate, variable and/or tapered. In some embodiments, the outer surface of shaft 38 may include one or a plurality of openings. In some embodiments, all or only a portion of the outer surface of shaft 38 may have alternate surface configurations to enhance fixation with tissue, such as, for example, rough, arcuate, undulating, mesh, porous, semi-porous, dimpled and/or textured. In some embodiments, all or only a portion of shaft 38 may be disposed at alternate orientations, relative to its longitudinal axis, such as, for example, transverse, perpendicular and/or other angular orientations such as acute or obtuse, co-axial and/or may be offset or staggered. In some embodiments, all or only a portion of shaft 38 may be cannulated.

In assembly, operation and use, surgical system 30, similar to the systems and methods described herein, includes inserter 32 and/or implants disposed therewith, and is employed with a surgical procedure for treatment of a spinal disorder affecting a section of a spine of a patient, as discussed herein. The components of surgical system 30 are employed with a surgical procedure for treatment of a condition or injury of an affected section of the spine, such as, for example, vertebrae.

In use, to treat a selected section of vertebrae, a medical practitioner obtains access to a surgical site in any appropriate manner, such as through incision and retraction of tissues. In some embodiments, surgical system 30 can be used in any existing surgical method or technique including open surgery, mini-open surgery, minimally invasive surgery and percutaneous surgical implantation, whereby vertebrae are accessed through a mini-incision, or sleeve that provides a protected passageway to the area. Once access to the surgical site is obtained, the particular surgical procedure can be performed for treating the spine disorder.

An incision is made in the body of a patient and a cutting instrument creates a surgical pathway for implantation of components of surgical system 30. A preparation instrument can be employed to prepare tissue surfaces of vertebrae as well as for aspiration and irrigation of a surgical region.

Figure 11:
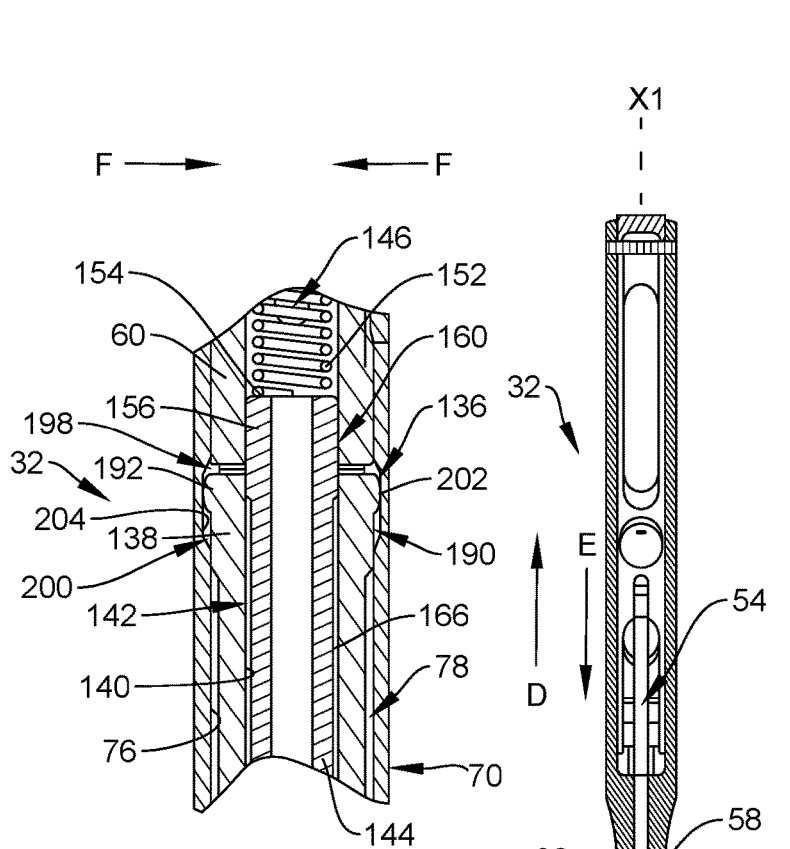
FIG. 11 is an enlarged, cross section view of the surgical instrument shown in FIG. 1 at detail A in FIG. 10.
Figure 12:
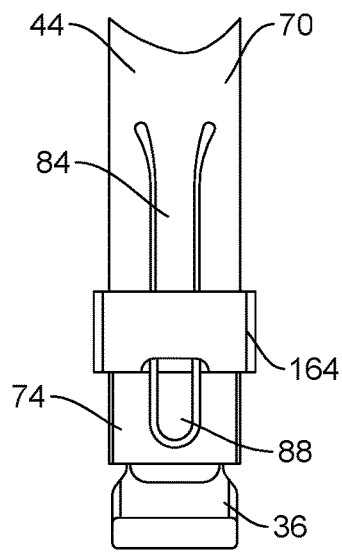
FIG. 12 is a side view of components of the surgical instrument shown in FIG. 1, with the surgical instrument in the first position.
Figures 9, 10:
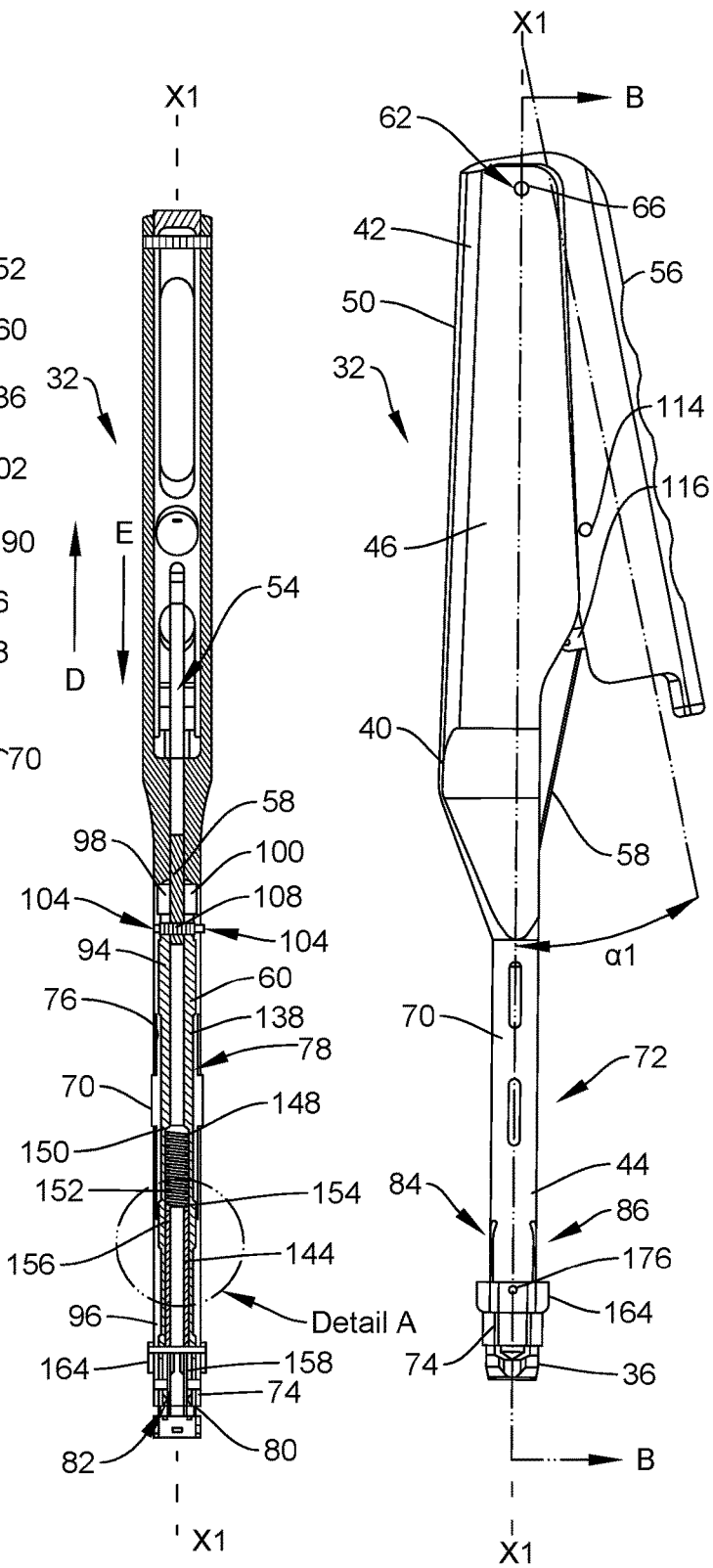
FIG. 9 is a third side view of the surgical instrument shown in FIG. 1, with the surgical instrument in a first position.
FIG. 10 is a fourth side, cross sectional view of the surgical instrument shown in FIG. 1 taken along lines B-B in FIG. 9.
Figure 12A:
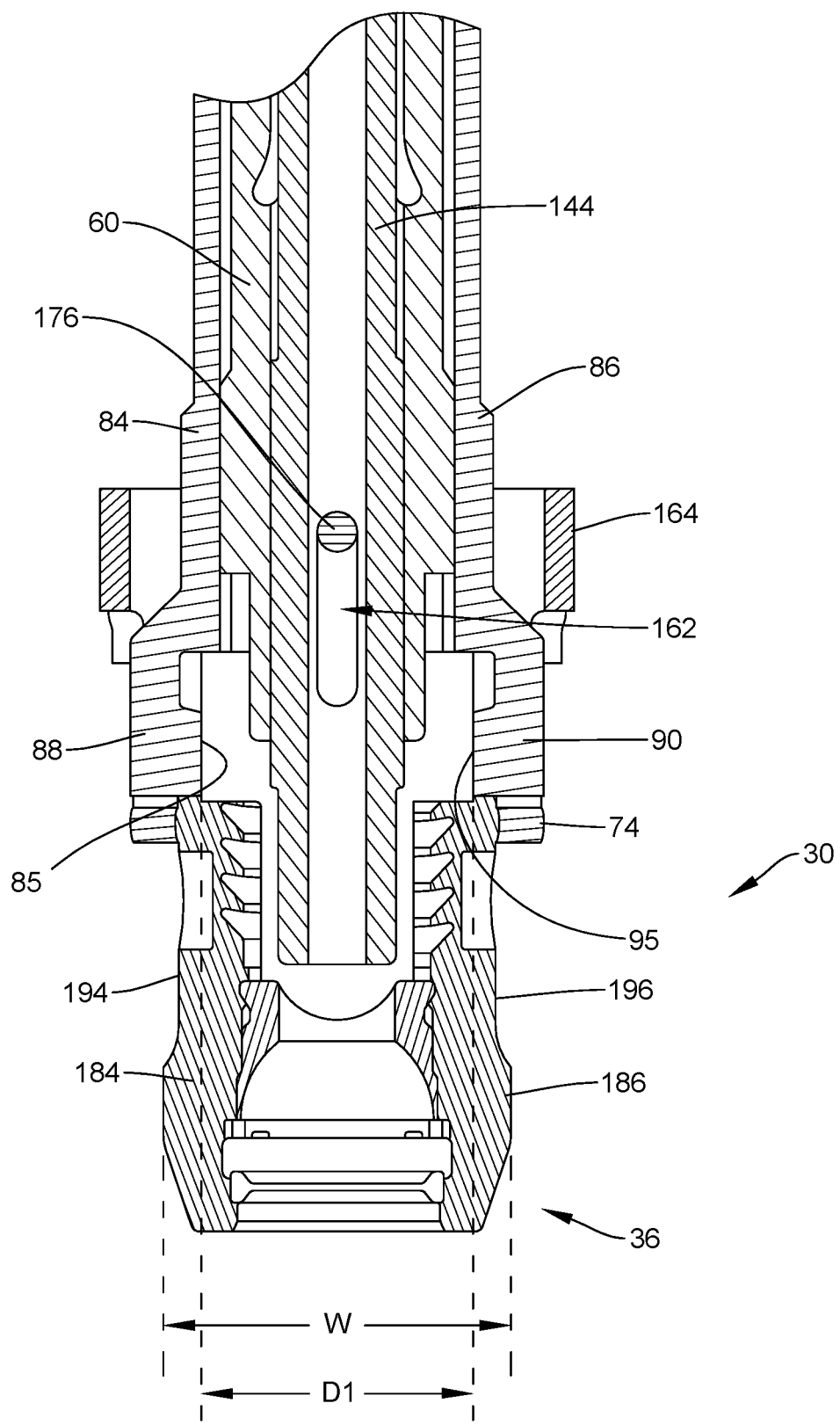
FIG. 12A is a side, cross sectional view of components of the surgical instrument shown in FIG. 1, with the surgical instrument in the first position.
Figure 22:
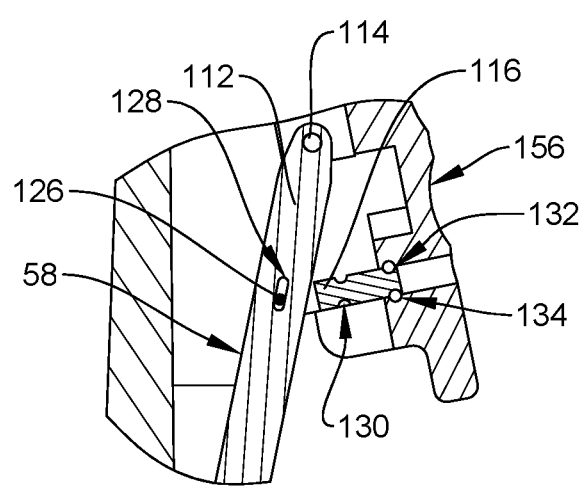
FIG. 22 is a side, cross section view of components of the surgical instrument shown in FIG. 1, with the surgical instrument in the first position.

Pilot holes are made in selected levels of vertebrae for receiving one or more screw shafts 38. Inserter 32 is delivered to the surgical region with inserter 32 in the first, open position such that handle 56 is disposed at an angle $\alpha 1$ relative to axis X1, as shown in FIG. 9. Spring 134 is not positioned in groove 130 or groove 132, as shown in FIG. 22. When inserter 32 is in the first, open position, plunger 144 is in a down position, as shown in FIGS. 10 and 11. When plunger 144 is in the down position, spring tab 136 is positioned in an internal bore 190 of shaft 72, surface 160 directly engages surface 140 of spring tab 136, an outer surface 202 of a lip 192 of spring tab 136 directly engages an inner surface 204 of shaft 72 that defines bore 190, and surface 160 directly engages surface 140 to prevent or block spring tab 136 from deflecting inwards, such as, for example, the direction shown by arrows F in FIG. 11. In some embodiments, lip 192 is positioned in bore 190 when plunger 144 is in the down position. Bore 190 has a length that is greater than a height of lip 192 such that lip 192 can translate relative to body 40 along axis X1 in the direction shown by arrow D and/or the direction shown by arrow E within bore 190. When inserter 32 is in the first, open position, sleeve 164 is in an up position as shown in FIG. 12. When sleeve 164 is in the up position, an inner surface 85 of end 88 of spring tab 84 is spaced apart a first distance from an inner surface 95 of end 90 of spring tab 86, as shown in FIG. 12A. In some embodiments, tulip head 36 has a width W defined by the distance from an outer surface 194 or arm 184 to an outer surface 196 of arm 186 that is less than a first distance D1 from inner surface 85 to inner surface 95 such that head 36 can be inserted between ends 88, 90 and/or removed from cavity 82. In some embodiments, width W is equal to or greater than first distance D1 such that the distance between inner surface 85 and inner surface 95 must be increased to insert head 36 between inner surface 85 and inner surface 95, as discussed herein.

Figure 23:
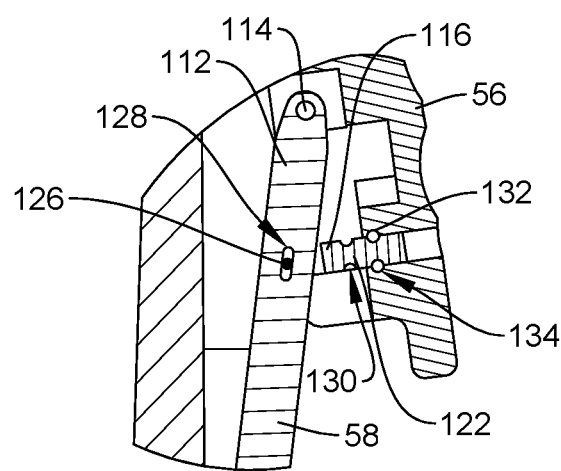
FIG. 23 is a side, cross section view of components of the surgical instrument shown in FIG. 1, with the surgical instrument in the second position.

Inserter 32 is moved from the first, open position to the second, secured position by squeezing handle 56 to move handle 56 toward body 40 such that handle 56 is disposed at an angle $\alpha 2$ relative to axis X1, as shown in FIG. 13. Angle $\alpha 2$ is less than angle $\alpha 1$. As handle 56 moves toward body 40, spring 134 moves into groove 132, as shown in FIG. 23.

Figure 16A:
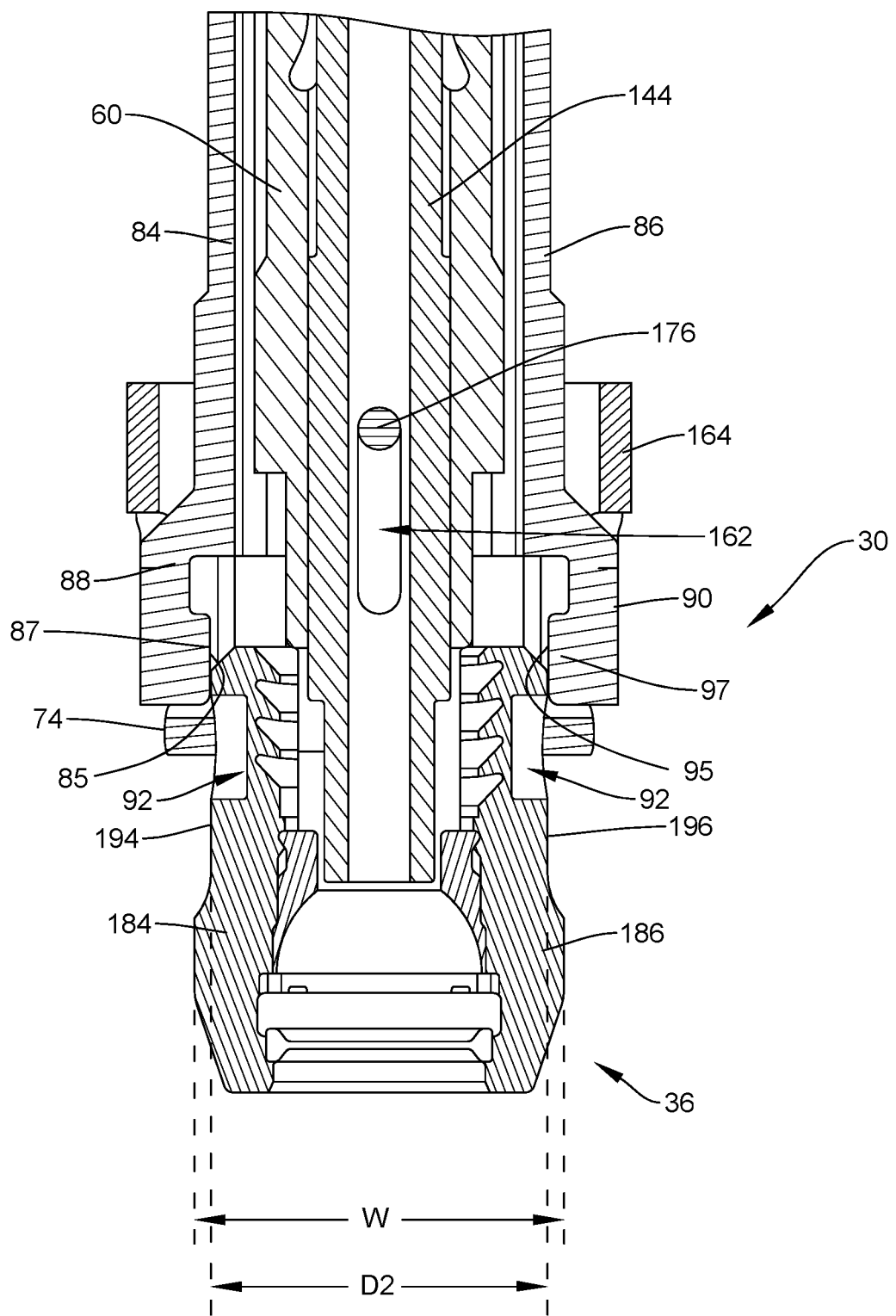
FIG. 16A is a side, cross sectional view of components of the surgical instrument shown in FIG. 1, with the surgical instrument in the second position.

When inserter 32 in the second, secured position, plunger 144 is in the down position such that lip 192 of spring tab 136 is positioned in bore 190, as shown in FIGS. 14 and 15. In some embodiments, lip 192 moves from an upper portion 198 of bore 190 to a lower portion 200 of bore 190 as inserter 32 moves from the first, open position to the second, secured position. When inserter 32 in the second, secured position, plunger 144 is in the down position such that surface 160 directly engages surface 140 of spring tab 136 and surface 202 of lip 192 directly engages surface 204 of shaft 72 to prevent or block spring tab 136 from deflecting inwards, such as, for example, the direction shown by arrows F in FIG. 11. Lip 192 is positioned in portion 200 of bore 190 to prevent pusher 60 from translating relative to body 40 along axis X1 in the direction shown by arrow E in FIG. 11. When inserter 32 in the second, secured position, sleeve 164 is in a secured position, as shown in FIG. 16. Sleeve 164 moves relative to body 40 in the direction shown by arrow E to move sleeve 164 from the up position to the secured position. When sleeve 164 is in the secured position, inner surface 85 of end 88 of spring tab 84 is spaced apart a second distance D2 from inner surface 95 of end 90 of spring tab 86. Second distance D2 is greater than first distance D1 to allow inner surfaces 85, 95 to translate over and engage outer surfaces 194, 196, respectively. That is, width W is less than or equal to second distance D2 such that inner surfaces 85, 95 of ends 88, 90 directly engage arms 184, 186 to secure head 36 to body 40 in a manner that prevents body 40 from disengaging head 36. In some embodiments, projections 87, 97 that define inner surfaces 85, 95 of ends 88, 90 are spaced apart from recesses 92 of arms 184, 186 when inserter 32 is in the second, secured position.

Figure 19:
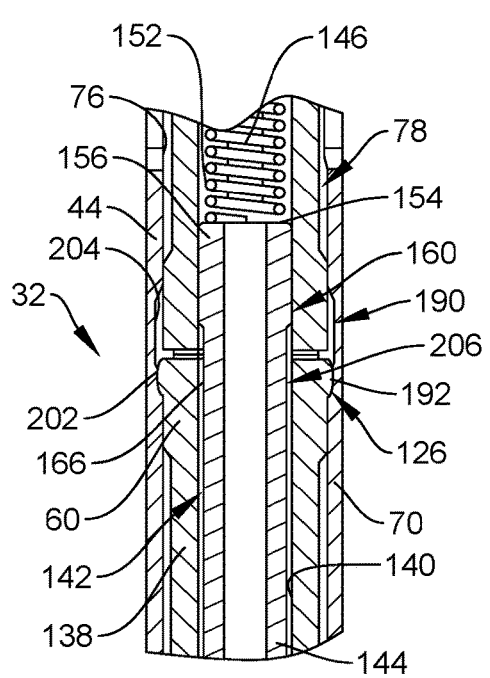
FIG. 19 is an enlarged, cross section view of the surgical instrument shown in FIG. 1 at detail C in FIG. 18.
Figure 20:
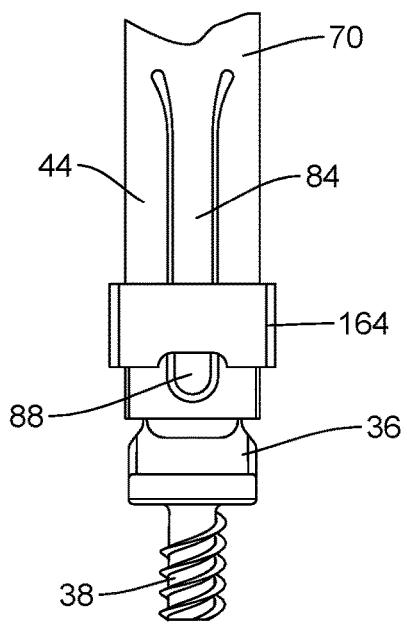
FIG. 20 is a side view of components of the surgical instrument shown in FIG. 1 with the surgical instrument in the third position.
Figure 18:
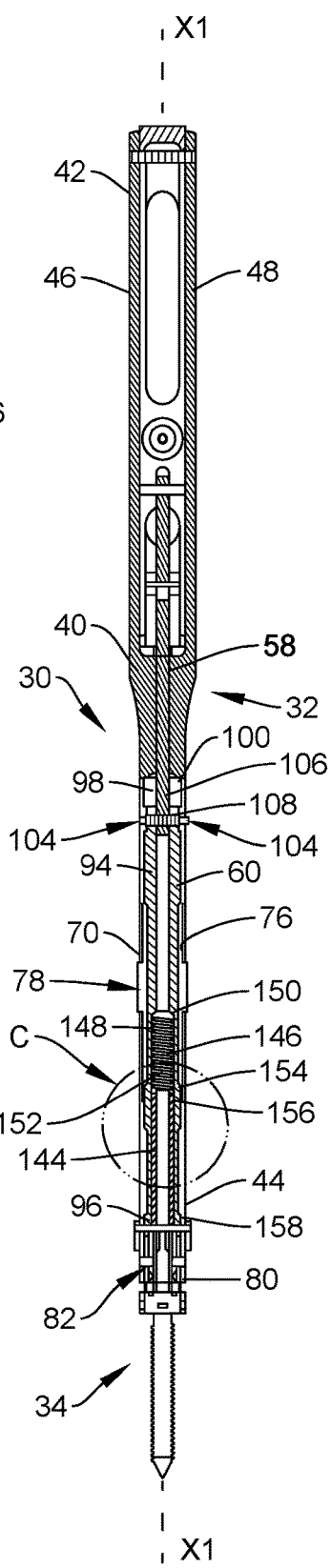
FIG. 18 is a side, cross sectional view of the surgical instrument shown in FIG. 1 taken along lines D-D in FIG. 17.
Figure 17:
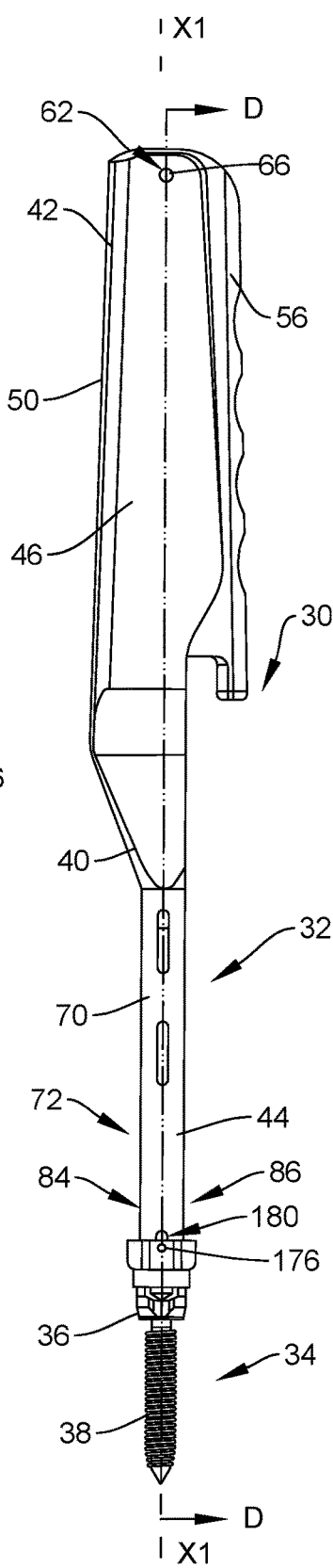
FIG. 17 is a fifth side view of the surgical instrument shown in FIG. 1, with the surgical instrument in a third position.
Figure 20A:
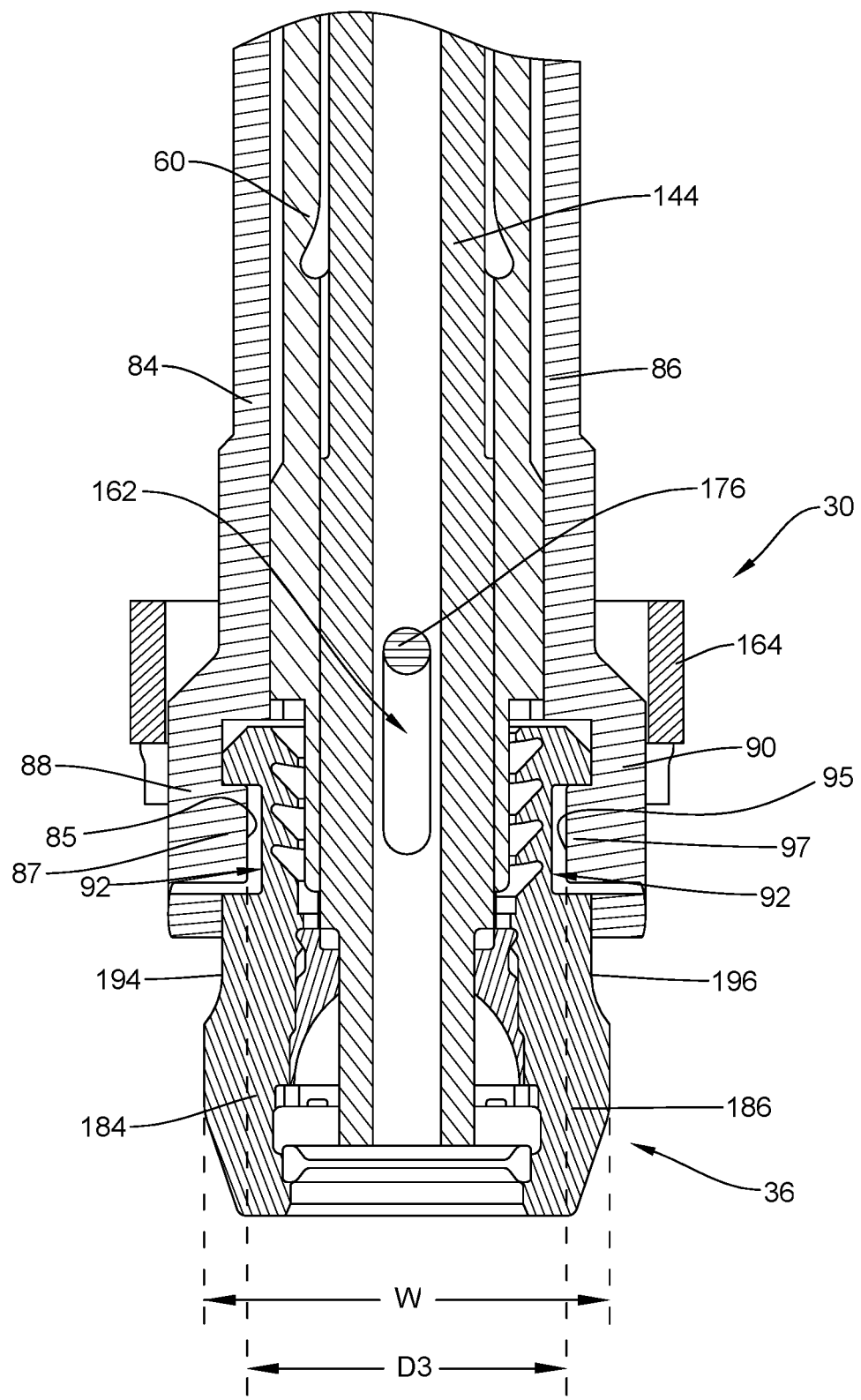
FIG. 20A is a side, cross sectional view of components of the surgical instrument shown in FIG. 1 with the surgical instrument in the third position.
Figure 24:
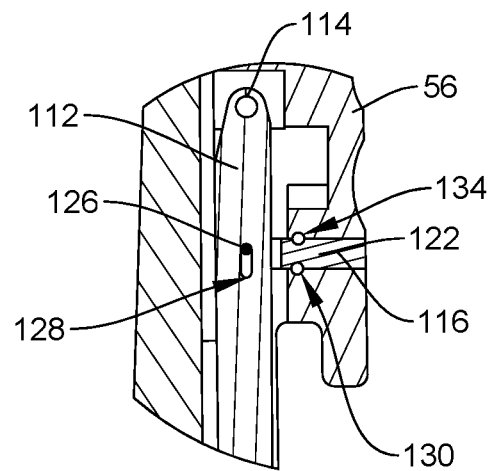
FIG. 24 is a side, cross section view of components of the surgical instrument shown in FIG. 1, with the surgical instrument in the third position.

Inserter 32 is moved from the second, secured position to the third, attachment position by squeezing handle 56 to move handle 56 toward body 40 such that handle 56 extends parallel to axis X1, as shown in FIG. 17. As handle 56 moves toward body 40, spring 134 moves out of groove 132 and into groove 130, as shown in FIG. 24. In some embodiments, the tapered configuration of groove 130 allows spring 134 to change shape after spring 134 moves into groove 130 to allow spring 134 to move out of groove 130 and into the configuration when inserter 32 is in the first, open position such that spring 134 is not positioned in groove 130 or groove 132, as shown in FIG. 22. When inserter 32 in the third, attachment position, plunger 144 is in an up position such that lip 192 of spring tab 136 is positioned distal to bore 190, as shown in FIGS. 18 and 19. When plunger 144 is in the up position, surface 160 is spaced apart from surface 140 of spring tab 136 and there is a gap 206 between surface 166 of plunger 144 and surface 140 of spring tab 136 such that spring tab 136 is capable of deflecting inwards, such as, for example, the direction shown by one of arrows F in FIG. 11. When inserter 32 in the third, attachment position, sleeve 164 is in a fully down position, as shown in FIG. 20. Sleeve 164 moves relative to body 40 in the direction shown by arrow E to move sleeve 164 from the secured position to the fully down position. When sleeve 164 is in the fully down, inner surface 85 of end 88 of spring tab 84 is spaced apart a third distance D3 from inner surface 95 of end 90 of spring tab 86. Third distance D3 is less than second distance D2. In some embodiments, width W of head 36 is less than third distance D3 such that ends 88, 90 directly engage arms 184, 186 to secure head 36 to body 40 in a manner that prevents body 40 from disengaging head 36 unintentionally. In some embodiments, projections 87, 97 are positioned in recesses 92 of arms 184, 186 when inserter 32 in the third, attachment position to fix head 36 to inserter 32. In some embodiments, third distance D3 is equal to first distance D1. In some embodiments, third distance D3 is less than first distance D1. In some embodiments, third distance D3 is greater than first distance D1.

With head 36 positioned in cavity 82 an inserter 32 in the third, attachment position, inserter 32 is manipulated to position head 36 adjacent to shaft 38, which has been implanted in one of the vertebrae. An aperture of head 36 is aligned with shaft 38 and inserter 32 is manipulated to insert shaft 38 into the aperture of head 36 to connect head 36 with shaft 38. In some embodiments, head 36 is configured to snap onto shaft 38 to prevent head 36 from unintentionally being removed from shaft 38. In some embodiments, a spinal construct, such as, for example, a spinal rod is inserted into passageway 188 and a set screw is threaded with the threads on the inner surfaces of arms 184, 186 until the set screw directly engages the spinal rod within passageway 188 to fix the spinal rod relative to head 36.

Upon completion of a procedure, as described herein, the surgical instruments, assemblies and non-implanted components of surgical system 30 are removed and the incision(s) are closed. One or more of the components of surgical system 30 can be made of radiolucent materials such as polymers. Radiomarkers may be included for identification under x-ray, fluoroscopy, CT or other imaging techniques. In some embodiments, surgical system 30 may include one or a plurality of spinal rods, plates, connectors and/or bone fasteners for use with a single vertebral level or a plurality of vertebral levels.

In some embodiments, one or more bone fasteners, as described herein, may be engaged with tissue in various orientations, such as, for example, series, parallel, offset, staggered and/or alternate vertebral levels. In some embodiments, the bone fasteners may comprise multi-axial screws, sagittal adjusting screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, surgical system 30 includes an agent, which may be disposed, packed, coated or layered within, on or about the components and/or surfaces of surgical system 30. In some embodiments, the agent may include bone growth promoting material, such as, for example, bone graft to enhance fixation of the components and/or surfaces of surgical system 30 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
   a first member defining a passageway, the first member comprising a first lock and a second lock;
   a second member positioned in the passageway, the second member comprising a lumen and a spring tab;
   a third member coupled to the second member; and
   a fourth member positioned in the lumen of the second member, the fourth member being movable relative to the second member between a first orientation in which the fourth member prevents the spring tab from deflecting inwardly and a second orientation in which the spring tab is allowed to deflect inwardly,
wherein the second member is coupled to the third member and movable relative to the first member to move the third member between a first position in which the first lock is spaced a first distance apart from the second lock, and a second position in which the first lock is spaced a second distance apart from the second lock, the second distance being less than the first distance.

2. The surgical instrument recited in claim 1, wherein the third member translates axially along the first member as the third member moves between the first position and the second position.

3. The surgical instrument recited in claim 1, wherein the second member is coupled with the third member such that the third member translates with the second member as the second member translates relative to the first member.

4. The surgical instrument recited in claim 1, wherein at least one of the locks comprises a spring tab.

5. The surgical instrument recited in claim 1, further comprising a fourth member and a link joining the fourth member to the second member, the fourth member being pivotable relative to the first member to move the third member from the first position to the second position.

6. The surgical instrument recited in claim 1, wherein the third member is prevented from moving from the first position to the second position when the fourth member is in the first orientation.

7. The surgical instrument recited in claim 1, wherein the third member is movable between the first position and the second position when the fourth member is in the second orientation.

8. The surgical instrument recited in claim 1, wherein a pin extends through the second member, the third member and the fourth member.

9. A surgical instrument comprising:
an inserter body comprising a shaft defining a passageway, the shaft comprising a first spring tab and a second spring tab;
a pusher positioned in the passageway; and
a sleeve coupled to the pusher,
wherein the pusher is movable relative to the inserter body to move the sleeve between a first position in which the first spring tab is spaced a first distance apart from the second spring tab, and a second position in which the first spring tab is spaced a reduced second distance apart from the second spring tab.

10. The surgical instrument recited in claim 9, further comprising a handle coupled to the pusher by a link, the handle being pivotable relative to the inserter body to move the sleeve from the first position to the second position.

11. The surgical instrument recited in claim 9, further comprising a plunger positioned in a lumen of the pusher, the plunger being movable relative to the pusher between a first orientation in which the plunger prevents a spring tab of the pusher from deflecting inwardly and a second orientation in which the spring tab of the pusher is allowed to deflect inwardly.

12. The surgical instrument recited in claim 11, wherein the sleeve is prevented from moving from the first position to the second position when the plunger is in the first orientation.

13. The surgical instrument recited in claim 11, wherein the sleeve is movable between the first position and the second position when the plunger is in the second orientation.

14. The surgical instrument recited in claim 11, wherein a pin extends through the pusher, the sleeve and the plunger.

15. A surgical system comprising:
a surgical instrument comprising:
a first member defining a passageway, the first member comprising a first lock and a second lock,
a second member positioned in the passageway, the second member comprising a lumen and a spring tab,
a third member coupled to the second member, and
a fourth member positioned in the lumen of the second member, the fourth member being movable relative to the second member between a first orientation in which the fourth member prevents the spring tab from deflecting inwardly and a second orientation in which the spring tab is allowed to deflect inwardly; and
an implant comprising a head,
wherein the second member is movable relative to the first member to move the third member between a first position in which the first lock is spaced a first distance apart from the second lock to allow the head to be inserted into the passageway, and a second position in which the lock is spaced a reduced second distance apart from the second lock such that the locks engage the head within the passageway to fix the head relative to the shaft.

16. The surgical system recited in claim 15, wherein the second member is movable relative to the first member to move the third member between the second position and a third position in which the lock is spaced a third distance apart from the second lock, the third distance being less than the second distance.

17. The surgical system recited in claim 15, wherein the third member is disposed at a first location along the first member when the third member is in the first position and is disposed at a second location along the first member when the third member is in the second position, the second location being distal to the first location.

18. The surgical system recited in claim 15, further comprising a fourth member and a link joining the fourth member to the second member, the fourth member being pivotable relative to the first member to move the third member from the first position to the second position.

19. The surgical system recited in claim 15, wherein the head includes spaced apart arms, the arms defining an implant cavity therebetween, the locks each engaging one of the arms when the third member is in the second position.

20. The surgical system recited in claim 15, wherein the third member translates axially along the first member as the third member moves between the first position and the second position.

* * * * *